United States Patent [19]

Sugimori et al.

[11] Patent Number: 4,661,283

[45] Date of Patent: Apr. 28, 1987

[54] BENZOATE DERIVATIVES HAVING A LARGE POSITIVE DIELECTRIC ANISOTROPY VALUE AND LIQUID CRYSTAL COMPOSITIONS CONTAINING SAME

[75] Inventors: Shigeru Sugimori, Fujisawashi; Yasuyuki Goto, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 706,609

[22] Filed: Feb. 28, 1985

[30] Foreign Application Priority Data

Mar. 2, 1984 [JP] Japan .................................. 59-40029
Jul. 25, 1984 [JP] Japan ................................ 59-154277

[51] Int. Cl.$^4$ ...................... C09K 19/30; C09K 19/20; C07C 121/60
[52] U.S. Cl. ........................... 252/299.63; 252/299.67; 252/299.01; 558/416; 350/350 R
[58] Field of Search ...................... 252/299.63, 299.64, 252/299.67, 299.6, 299.01; 260/465 D, 465 G; 558/416; 350/350 R

[56] References Cited

U.S. PATENT DOCUMENTS

| | | | |
|---|---|---|---|
| 4,198,312 | 4/1980 | Sato et al. ........................ | 252/299.67 |
| 4,372,871 | 2/1983 | Toriyama et al. ............. | 252/299.63 |
| 4,424,371 | 1/1984 | Hsu ................................... | 252/299.67 |
| 4,452,719 | 6/1984 | Inoue et al. ...................... | 252/299.63 |
| 4,455,261 | 6/1984 | Sasaki et al. .................... | 252/299.67 |
| 4,551,280 | 11/1985 | Sasaki et al. .................... | 252/299.65 |
| 4,564,694 | 1/1986 | Hirai et al. ...................... | 252/299.64 |

FOREIGN PATENT DOCUMENTS 58-121266 7/1983 Japan .............................. 252/299.67
58-210982 12/1983 Japan .............................. 252/299.67

OTHER PUBLICATIONS

Kelly et al., CA 102: 54262, 1985.
Kelly et al., CA 102: 78517, 1985.

*Primary Examiner*—Teddy S. Gron
*Assistant Examiner*—J. E. Thomas
*Attorney, Agent, or Firm*—Wenderoth, Lind & Ponack

[57] ABSTRACT

A novel organic compound usable as a component of liquid crystal compositions having a positive value of dielectric anisotropy and a liquid crystal composition usable as a material for liquid-crystalline display devices operated under a low driving voltage are provided which compound is a benzoic acid ester derivative expressed by the formula

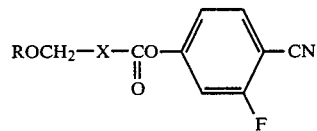

wherein R represents an alkyl group of 1 to 10 carbons and X represents

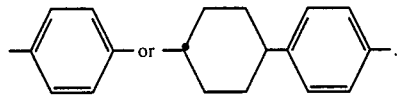

4 Claims, No Drawings

BENZOATE DERIVATIVES HAVING A LARGE POSITIVE DIELECTRIC ANISOTROPY VALUE AND LIQUID CRYSTAL COMPOSITIONS CONTAINING SAME

BACKGROUND OF THE INVENTION

1. Field of the Invention

This invention relates to a novel organic compound and more particularly to a novel organic compound usable as a component of liquid crystal compositions having a positive value of dielectric anisotropy.

2. Description of the Prior Art

Display elements using liquid crystals utilize the optical anisotropy and dielectric anisotropy of liquid-crystalline substances, and liquid-crystalline phases include nematic phase, smectic phase and cholesteric phase. Currently, display elements using nematic liquid crystals among those of the above phases have most widely been practically used. Such display elements include those of the TN type, DS type, guest-host type, etc., and properties required for liquid crystal compounds used for those of the respective types vary.

Anyhow, as for liquid crystal compounds used for these display elements, there are preferable those which exhibit the liquid-crystalline phase in a temperature range as broad as possible, and also they have been required to be stable to moisture, light, heat, air, etc.

Now, however, there is no single substance which satisfies such conditions; hence it is the present status that several kinds of liquid crystal compounds are employed and if required, non-crystalline compounds have been admixed for practical use.

U.S. Pat. No. 4,198,312 discloses compounds expressed by the formula

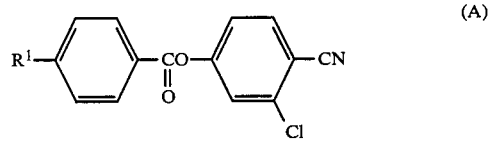

(A)

wherein $R^1$ represents an alkyl group of 1~9 carbons, and U.S. Pat. No. 4,452,719 discloses compounds expressed by the formula

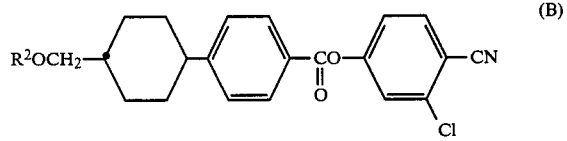

(B)

wherein $R^2$ represents an alkyl group of 1~10 carbons. However, the compounds of the formula (A) exhibit no liquid-crystalline phase and have high viscosities; hence when used for liquid crystal materials, they have a drawback of narrowing the mesomorphic range of the resulting liquid crystal composition. Further, the compounds of the formula (B) have relatively narrow mesomorphic ranges and relatively high viscosities; hence there is a certain extent of drawback for using them as a component of liquid crystal compositions.

SUMMARY OF THE INVENTION

An object of the present invention is to provide a novel organic compound suitable for being used as a component of liquid-crystalline dielectrics. Another object of the present invention is to provide a liquid crystal composition for being used as a material for liquid-crystalline display devices operated under low driving voltages. These objects are achieved by compounds and liquid crystal compositions described below.

(1) The present invention resides, in a first aspect, in benzoic acid ester derivatives expressed by the formula

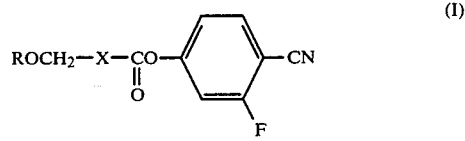

(I)

wherein R represents an alkyl group of 1 to 10 carbon atoms and X represents

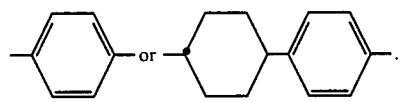

(2) An embodiment of the above derivatives resides in 3-fluoro-4-cyanophenyl 4-alkoxymethylbenzoates as the derivatives of the formula (I) wherein X represents

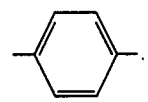

(3) Another embodiment of the above derivatives resides in 3-fluoro-4-cyanophenyl 4-(trans-4-alkoxymethylcyclohexyl)benzoates as the derivatives of the formula (I) wherein X represents

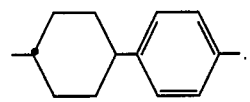

(4) The present invention resides, in a second aspect, in a liquid crystal composition having at least two components at least one of which is selected from benzoic acid ester derivatives expressed by the above formula (I).

DETAILED DESCRIPTION OF THE PREFERRED EMBODIMENTS

The compounds of the present invention expressed by the formula (I) can be prepared by reacting a reactive derivative of carboxylic acids of the following formula (II) (preferably the corresponding carboxylic acid chlorides) with a 3-fluoro-4-cyanophenol of the following formula (III):

ROCH$_2$—X—COOH (II)

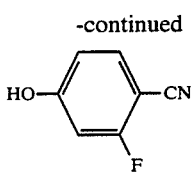
(III)

R and X in the formula (II) are as defined above, and R and X in the formulas described in the specification are also as defined above unless otherwise indicated.

The above ester formation reaction may be carried out generally at a temperature of 0° C. to about 100° C., preferably 30° C. to 80° C. in an inert solvent such as benzene or toluene. Further, it is preferred to add a base such as pyridine or triethylamine to the reaction system to thereby neutralize hydrogen chloride formed during the reaction. The compounds of the formula (II) are known and may be prepared according to the methods disclosed in U.S. Pat. No. 4,452,719 and Japanese patent application laid-open No. Sho 57-77,658 (1982). The preparations of the compounds of the formula (II) and those of the formula (III) will be described below.

First, α-bromo-p-tolunitrile (IV) is reacted with a sodium alcoholate to obtain an α-alkoxy-p-tolunitrile (V) which is then hydrolyzed with an alkali aqueous solution to obtain a 4-alkoxymethylbenzoic acid (IIa). These reactions are illustrated in scheme 1 shown later.

Further, 4-(trans-4-alkoxymethylcyclohexyl)-benzoic acids (IIb) may be prepared using methyl trans-4-phenylcyclohexylcarboxylate (VI) as a starting raw material as follows:

The compound (VI) has been reported by W. S. Johnson et al (J. Am. Ch. Soc., 67, 1045 (1945)). The compound (VI) is reduced with a reducing agent such as lithium aluminum hydride to obtain trans-4-phenyl-cyclohexylmethanol (VII) which is then reacted with p-toluenesulfonyl chloride in dry pyridine to obtain trans-4-phenylcyclohexylmethyl p-toluenesulfonate (VIII) which is then reacted with an alkali alcoholate to obtain a trans-4-alkoxymethyl-1-phenylcyclohexane (IX) which is heated with iodine and iodic acid in a basic solvent such as dimethylformamide to obtain a 4-(trans-4-alkoxymethylcyclohexyl)-1-iodobenzene (X) which is then reacted with a cyanogenating agent such as cuprous cyanide to obtain a 4-(trans-4-alkoxymethyl-cyclohexyl)-benzonitrile (XI) which is then hydrolyzed in the presence of an alkali to obtain a 4-(trans-4-alkoxymethylcyclohexyl)-benzoic acid (IIb). These reactions are illustrated in scheme 2 below.

Scheme 1

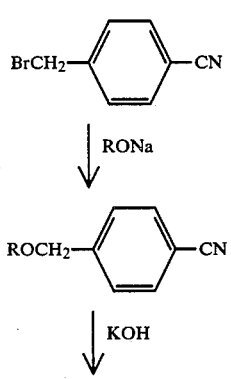

Scheme 1 (continued)

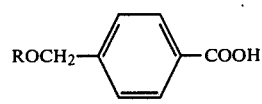
(IIa)

Scheme 2

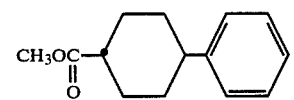
(VI)

↓ LiAlH₄

(VII)

↓ 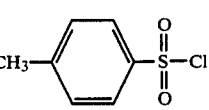

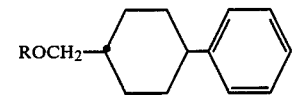
(VIII)

↓ RONa

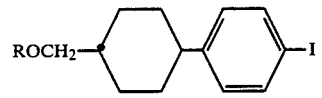
(IX)

↓ I₂, HIO₃

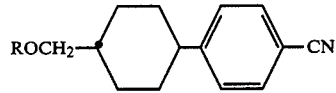
(X)

↓ CuCN

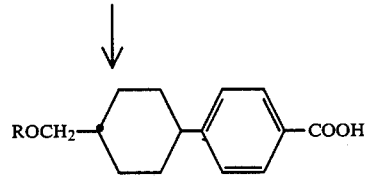
(XI)

↓

(IIb)

The above carboxylic acids of the formula (IIa) or the formula (IIb) can be easily converted into the corresponding acid chlorides by reacting the acids with thionyl chloride.

Further, 3-fluoro-4-cyanophenol (III) as another raw material may be obtained by dehydrating 2-fluoro-4-hydroxybenzaldoxime with acetic anhydride, followed by hydrolysis of the resulting acetate with an alkali.

In addition, preparation of the compounds of the present invention may be effected according to other known methods, besides the above preparation.

Among the compounds of the present invention, those of the formula (I) wherein R represents a linear chain alkyl group are preferred. Further, those of the formula (I) wherein R represents a branched alkyl group have a superior solubility in general-purpose liquid-crystalline materials; hence they are important in certain cases.

The compounds of the present invention are superior in compatibility with other liquid crystal compounds as described later and exhibit a large positive value of dielectric anistropy. Namely, when the compounds of the present invention are mixed with other liquid crystal compounds to form a liquid crystal composition, they function as if they were liquid crystal compounds having a large positive value of dielectric anisotropy to an extent of 40 to 50 at 25° C.; hence they are useful compounds for forming a liquid crystal composition imparting a low threshold voltage and saturation voltage. For example, as shown in Example 3 and Comparative example 1 as described below, addition of the compounds of the present invention leads to a great increase in the value of dielectric anistropy of liquid crystal compositions. This is presumed to be due to the effect of an alkoxymethyl group in place of the alkyl group $R^1$ in the aforementioned formula (A).

Further, 3-chloro-4-cyanophenyl 4-(trans-4-methoxymethylcyclohexyl)-benzonate as one of the compounds of the aforementioned formula (B) has a nematic phase temperature range as relatively narrow as 99.4° C.~137.0° C., while 3-fluoro-4-cyanophenyl 4-(trans-4-methoxymethylcyclohexyl)-benzoate shown in Example 2 described later has a nematic phase temperature range as broad as 109.3°~193.4° C. Thus, as shown in these examples, since the compounds of the present invention have broad nematic phase temperature ranges, they are useful as a component of liquid-crystalline materials.

The compounds of the present invention have low viscosities, and as shown in Example and Comparative example described later, liquid crystal compositions having the compounds added as a component have a very small increase in viscosity. This has been attained by replacing the chlorine atom of the compounds of the formula (A) and the formula (B) by fluorine atom.

The liquid crystal compositions of the present invention are preferred to contain the compounds of the present invention shown by the formula (I) in an amount of 1 to 30% by weight, preferably 5 to 20% by weight. If the content of the compounds of the present invention is less than 1% by weight, contribution of the compositions to dielectric anisotropy is small, while if the content exceeds 30% by weight, the viscosity of the compositions increases and thereby reduces their practical properties.

Existing liquid-crystalline compounds usable together with the compounds of the present invention in the liquid crystal compositions of the present invention are selected from the compounds belonging to the groups expressed by the following general formulas (i)~(xxxiii):

In these formulas, X represents

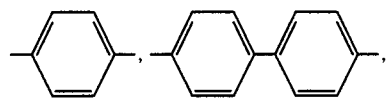

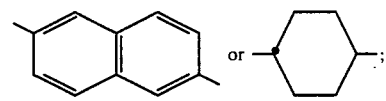

Y represents —CN, R', halogeno group or —COO-X-Y'; Y' represents —CN, R' or —OR'; and R and R' each represents an alkyl group.

Further, compounds of these formulas also include those wherein one hydrogen atom in benzene ring(s) is substituted by a halogen atom such as F.

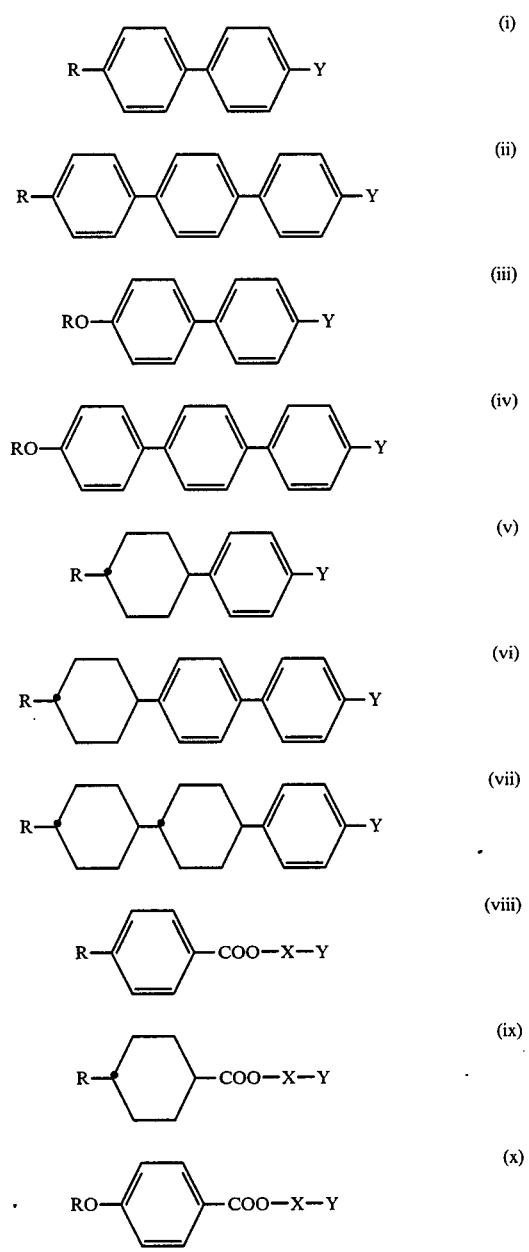

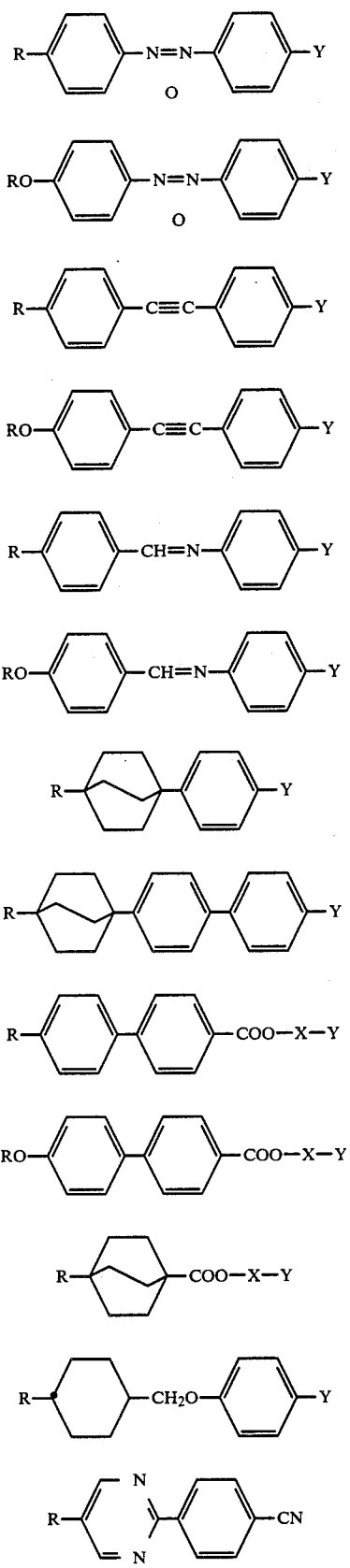
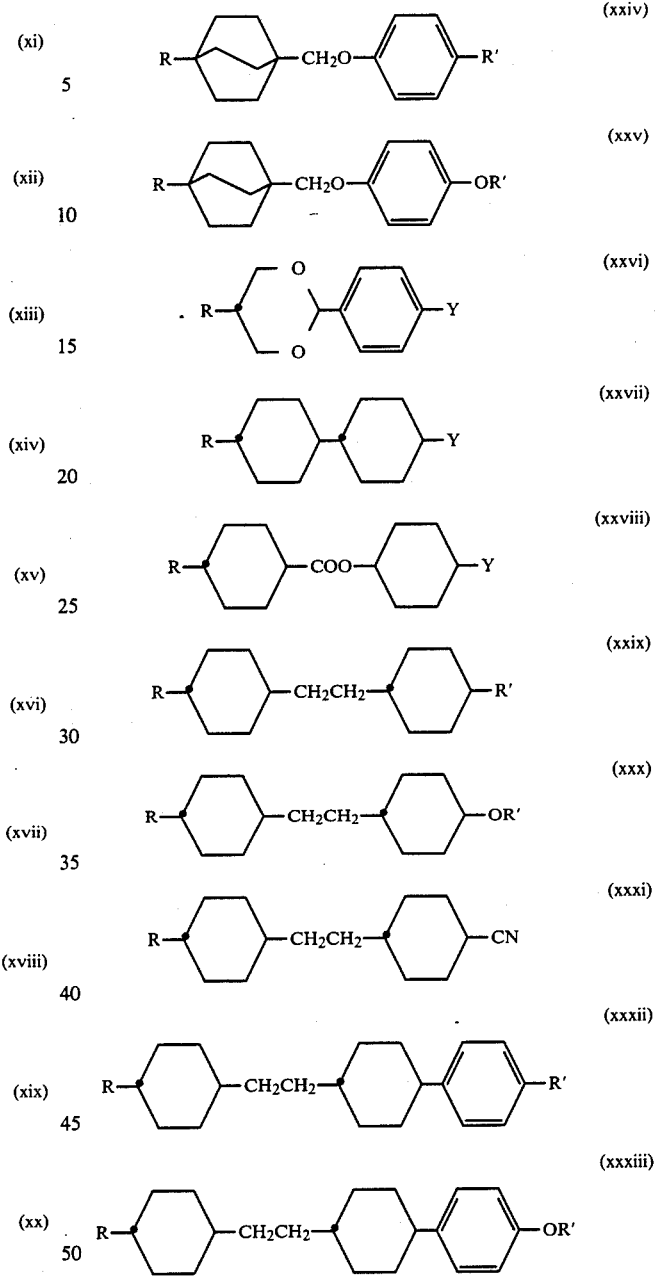

The present invention will be described in more detail by way of Examples, but it should not be construed to be limited thereto. In the following examples, melting point, crystalline-nematic phase transition point and nematic-clearing point are abbreviated to C-I point, C-N point and N-I point, respectively. Further, the value of dielectric anisotropy is abbreviated to Δε.

EXAMPLE 1

3-Fluoro-4-cyanophenyl 4-methoxymethylbenzoate

3-Fluoro-4-cyanophenol (1.5 g, 11 m mol) was dissolved in pyridine (5 ml) and to this solution was added a solution of methoxymethylbenzoyl chloride (2.3 g, 11 m mol) dissolved in dry toluene (10 ml), followed by reacting the mixture on heating at 60° C. for 3 hours. After completion of the reaction, the reaction mixture was fed into water (100 ml), followed by separating the resulting toluene layer, washing it with 6N—HCl, 2N—NaOH aqueous solution and then water, drying the toluene layer over anhydrous sodium sulfate, distilling off toluene from the toluene layer and recrystallizing the remaining oily substance from ethyl alcohol (5 ml) to obtain the objective 3-fluoro-4-cyanophenyl 4-methoxymethylbenzoate (1.8 g) having a C-I point of 89.5° C. and a N-I point of 27.7° C. (monotropic).

In the same manner as above, the following compounds are obtained from the corresponding carboxylic acid chlorides:
3-fluoro-4-cyanophenyl 4-ethoxymethylbenzoate,
3-fluoro-4-cyanophenyl 4-propoxymethylbenzoate (C-I point 36.2° C., N-I point 1.3° C. (monotropic))
3-fluoro-4-cyanophenyl 4-butoxymethylbenzoate,
3-fluoro-4-cyanophenyl 4-pentyloxymethylbenzoate,
3-fluoro-4-cyanophenyl 4-hexyloxymethylbenzoate,
3-fluoro-4-cyanophenyl 4-heptyloxymethylbenzoate,
3-fluoro-4-cyanophenyl 4-octyloxymethylbenzoate,
3-fluoro-4-cyanophenyl 4-nonyloxymethylbenzoate, and
3-fluoro-4-cyanophenyl 4-decyloxymethylbenzoate.

EXAMPLE 2

3-Fluoro-4-cyanophenyl 4-(trans-4-methoxymethylcyclohexyl)-benzoate

3-Fluoro-4-cyanophenol (1.5 g, 11 m mol) was dissolved in dry pyridine (5 ml), and to this solution was added a solution of 4-(trans-4-methoxymethylcyclohexyl)benzoyl chloride (2.7 g, 11 m mol), dissolved in toluene (10 ml), followed by reacting the mixture on heating at 60° C. for 3 hours.

After completion of the reaction, the reaction mixture was fed into water (100 ml), followed by separating the resulting toluene layer, washing it with 6N—HCl, 2N—NaOH aqueous solution and then water, drying the toluene layer over anhydrous sodium sulfate, distilling off toluene from the toluene layer and recrystallizing the remaining solids from ethanol (8 ml) to obtain the objective 3-fluoro-4-cyanophenyl 4-(trans-4-methoxymethyl)-benzoate (2.7 g, yield 66%) having a C-N point of 109.3° C. and a N-I point of 193.4° C.

In the same manner as above, the following compounds are obtained from the corresponding carboxylic acid chlorides:
3-fluoro-4-cyanophenyl 4-(trans-4-ethoxymethylcyclohexyl)-benzoate,
3-fluoro-4-cyanophenyl 4-(trans-4-propoxymethylcyclohexyl)-benzoate,
3-fluoro-4-cyanophenyl 4-(trans-4-butoxymethylcyclohexyl)-benzoate (C-N point 45.2° C., N-I point 126.6° C.),
3-fluoro-4-cyanophenyl 4-(trans-4-pentyloxymethylcyclohexyl)-benzoate (C-N point 63.1° C., N-I point 122.1° C.),
3-fluoro-4-cyanophenyl 4-(trans-4-hexyloxymethylcyclohexyl)-benzoate,
3-fluoro-4-cyanophenyl 4-(trans-4-heptyloxymethylclo hexyl)-benzoate,
3-fluoro-4-cyanophenyl 4-(trans-4-octyloxymethylcyclohexyl)-benzoate,
3-fluoro-4-cyanophenyl 4-(trans-4-nonyloxymethylcyclohexyl)-benzoate, and
3-fluoro-4-cyanophenyl 4-(trans-4-decyloxymethylcyclohexyl)-benzoate.

EXAMPLE 3

A nematic liquid crystal composition A consisting of

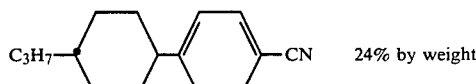 24% by weight

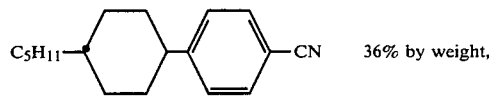 36% by weight,

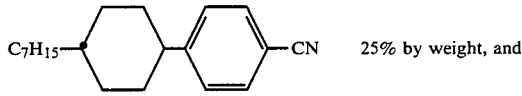 25% by weight, and

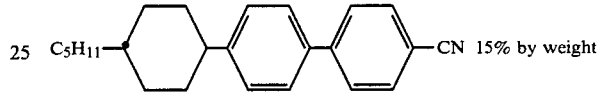 15% by weight has a N-I point of 72.0° C., a Δε of 11.6 and a viscosity at 20° C. of 28 cp. When this liquid crystal composition was sealed in a TN cell having a cell thickness of 10 μm, the operation threshold voltage and saturation voltage of the resulting cell were 1.75 V and 2.40 V, respectively.

When 3-fluoro-4-cyanophenyl 4-methoxymethylbenzoate as a compound of the present invention shown in Example 1 (10 parts by weight) was added to the above liquid crystal composition A (90 parts by weight), the resulting composition had a N-I point of 62.0° C., a Δε of 16.0 and a viscosity at 20° C. of 34 cp. When this composition was sealed in the above TN cell, the operation threshold voltage and saturation voltage of the resulting cell lowered down to 1.36 V and 2.00 V, respectively.

COMPARATIVE EXAMPLE 1

In place of 3-fluoro-4-cyanophenyl 4-methoxymethylbenzoate in Example 3, 3-chloro-4-cyanophenyl 4-propylbenzoate was added in 10% by weight to prepare a liquid crystal composition. This composition had a N-I point of 48° C., a Δε of 14.2 and a viscosity at 20° C. of 39 cp. When this composition was sealed in the same TN cell as in Example 3, the threshold voltage and saturation voltage were 1.51 V and 2.13 V, respectively.

From the foregoing, it is seen that when the compound of the present invention is added to the composition, there is exhibited a notable effectiveness of reducing the driving voltage of the liquid crystal composition.

EXAMPLE 4

A nematic liquid crystal composition consisting of

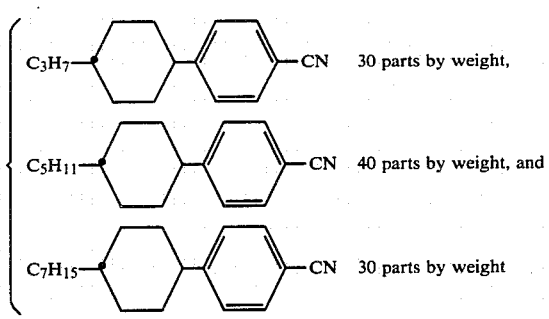

has a mesomorphic range of −5° C.–52.1° C., a Δε of 11.2 and a viscosity at 20° C. of 23.4 cp. When this liquid crystal composition was sealed in a TN cell having a cell thickness of 10 μm, the operation threshold voltage and saturation voltage of the resulting cell were 1.54 V and 2.13 V, respectively.

When 3-fluoro-4-cyanophenyl 4-(trans-4-methoxymethylcyclohexyl)-benzoate as a compound of the present invention shown in Example 2 (15 parts by weight) was added to the above liquid crystal composition (85 parts by weight), the resulting composition had a mesomorphic range extended to −10°–64° C., a Δε of 16.5 and a viscosity at 20° C. of 34 cp. When this composition was sealed in the above TN cell, the operation threshold voltage and saturation voltage of the resulting cell lowered down to 1.30 V and 1.90 V, respectively.

COMPARATIVE EXAMPLE 2

3-Fluoro-4-cyanophenyl 4-(trans-4-methoxymethylcyclohexyl)-benzoate in Example 4 was replaced by 3-chloro-4-cyanophenyl 4-(trans-4-methoxymethylcyclohexyl)-benzoate (15% by weight) to prepare a liquid crystal composition. This composition had a mesomorphic range extended to −3°–59.2° C., a Δε of 15.5 and a viscosity at 20° C. of 40 cp. When this composition was sealed in the same TN cell as used in Example 4, the threshold voltage and saturation voltage were 1.35 V and 1.90 V, respectively.

From the foregoing, it is seen that when the compound of the present invention is added to the composition, there is exhibited a notable effectiveness of extending the mesomorphic range of the composition and also reducing the driving voltage thereof.

What we claim is:

1. A benzoic acid ester derivative expressed by the formula

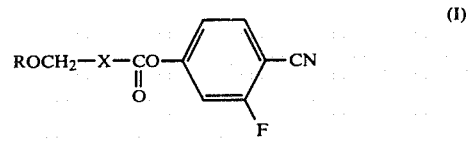

wherein R represents an alkyl group of 1 to 10 carbon atoms and X represents

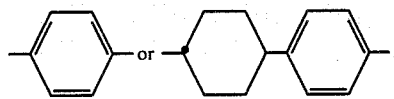

2. A 3-fluoro-4-cyanophenyl 4-alkoxymethylbenzoate according to claim 1 wherein X represents

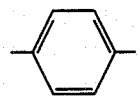

in the formula (I).

3. A 3-fluoro-4-cyanophenyl 4-(trans-4-alkoxymethylcyclohexyl)-benzoate according to claim 1 wherein X represents

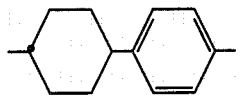

in the formula (I).

4. A liquid crystal composition having at least two components at least one of which is selected from benzoic acid ester derivatives expressed by the formula

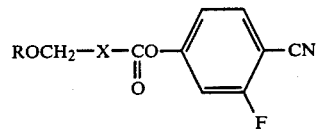

wherein R represents an alkyl group of 1 to 10 carbon atoms and X represents

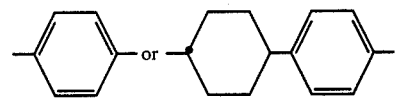

* * * * *